United States Patent
Mapstone et al.

(10) Patent No.: US 11,280,797 B2
(45) Date of Patent: Mar. 22, 2022

(54) METABOLIC BIOMARKERS FOR COGNITIVE ABILITY

(71) Applicants: Georgetown University, Washington, DC (US); University of Rochester, Rochester, NY (US)

(72) Inventors: Mark E. Mapstone, Irvine, CA (US); Howard J. Federoff, Irvine, CA (US); Massimo S. Fiandaca, Irvine, CA (US); Amrita K. Cheema, Potomac, MD (US)

(73) Assignees: Georgetown University, Washington, DC (US); University of Rochester, Rochester, NY (US)

( * ) Notice: Subject to any disclaimer, the term of this patent is extended or adjusted under 35 U.S.C. 154(b) by 34 days.

(21) Appl. No.: 16/483,260

(22) PCT Filed: Feb. 2, 2018

(86) PCT No.: PCT/US2018/016590
§ 371 (c)(1),
(2) Date: Aug. 2, 2019

(87) PCT Pub. No.: WO2018/144816
PCT Pub. Date: Aug. 9, 2018

(65) Prior Publication Data
US 2020/0011881 A1 Jan. 9, 2020

Related U.S. Application Data

(60) Provisional application No. 62/453,742, filed on Feb. 2, 2017.

(51) Int. Cl.
*G01N 33/68* (2006.01)

(52) U.S. Cl.
CPC ..... *G01N 33/6896* (2013.01); *G01N 2560/00* (2013.01); *G01N 2800/2814* (2013.01); *G01N 2800/50* (2013.01); *G01N 2800/52* (2013.01)

(58) Field of Classification Search
CPC ....... G01N 33/6896; G01N 2800/2814; G01N 2800/50
See application file for complete search history.

(56) References Cited

FOREIGN PATENT DOCUMENTS

WO WO 2016/187317 A1 11/2016

OTHER PUBLICATIONS

Mapstone, M. et al.) What success can teach us about failure: the plasma metabolome of older adults with superior memory and lessons for Alzheimer's disease. Neurobiology of Aging. Mar. 2017, Epub Nov. 21, 2016, vol. 51; pp. 148-155.
Mapstone, M. et al.) Plasma phospholipids identity antecedent memory impairment in older adults. Nature Medicine. Apr. 2014, Epub Mar. 9, 2014, vol. 20, No. 4; pp. 415-418.
Yi, J. et al.) L-Arginine and Alzheimer's Disease. International Journal of Clinical & Experimental Pathology. 2009, Epub Oct. 2, 2008, vol. 2, No. 3; pp. 211-238.
Corso, G. et al.) Serum Amino Acid Profiles in Normal Subjects and in Patients with or at Risk of Alzheimer Dementia. Dementia and Geriatric Cognitive Disorders Extra. May 4, 2017, vol. 7, No. 1; pp. 143-159.
International Search Report and Written Opinion dated Apr. 20, 2018 in corresponding International Application No. PCT/US2018/016590.

*Primary Examiner* — Olga N Chernyshev
(74) *Attorney, Agent, or Firm* — Grimes & Yvon LLP

(57) ABSTRACT

The present invention relates to methods of determining if a subject has a decreased risk of suffering from future memory impairment. The methods comprise analyzing at least one plasma sample from the subject to determine a value of the subject's metabolite profile and comparing the value of the subject's metabolite profile with the value of a normal metabolite profile. A change in the value of the subject's metabolite profile, over normal values is indicative that the subject has a decreased risk of suffering from future memory impairment compared to a normal individual.

13 Claims, 5 Drawing Sheets

METABOLIC BIOMARKERS FOR COGNITIVE ABILITY

CROSS-REFERENCE TO RELATED APPLICATIONS

This application is the National Stage entry under 35 U.S.C. § 371 of International Application No. PCT/US2018/016590 filed on Feb. 2, 2018, published on Aug. 9, 2018 under Publication No. WO 2018/144816 A1, which claims the benefit of U.S. Provisional Application No. 62/453,742 filed on Feb. 2, 2017, the entireties of which are herein incorporated by reference.

STATEMENT REGARDING FEDERALLY SPONSORED RESEARCH OR DEVELOPMENT

This invention was made with government support under grant number RO1 AG030753 awarded by the National Institutes of Health and under contract number W81XWH-09-1-0107 awarded by the Department of Defense. The government has certain rights in the invention.

BACKGROUND OF THE INVENTION

Field of the Invention

The present invention relates to methods of determining if a subject has a decreased risk of suffering from future memory impairment. The methods comprise analyzing at least one plasma sample from the subject to determine a value of the subject's metabolite profile and comparing the value of the subject's metabolite profile with the value of a normal metabolite profile. A change in the value of the subject's metabolite profile, over or under normal values is indicative that the subject has a decreased risk of suffering from future memory impairment compared to a normal individual.

BACKGROUND OF THE INVENTION

Aging is characterized by the progressive increase of inter-individual variability. This is especially evident in cognitive aging where the diversity of life experience and complexity of brain organization and function interact to produce individual cognitive trajectories. From the fourth decade of life onward, the most common cognitive trajectory is characterized by subtle decline in many abilities, but this is not invariant and relative stability and improvement is occasionally encountered into old age. These alternate trajectories may be supported by resistance to age-related accumulation of pathologies or cognitive reserve or enhanced neuroplasticity. Here, the plasma metabolome of older adults with superior memory was examined to seek new information about physiological processes supporting successful cognitive aging trajectories and to provide insights into age-related disorders such as Alzheimer's disease (AD), where memory impairment is the cardinal feature.

Continued interest in blood-based biomarkers remains because these specimens are obtained using minimally invasive, rapid, and relatively inexpensive methods. With recent technological advances in 'omics' technologies and systems biology analytic approaches, the comprehensive bioinformatic analyses of blood-based biomarkers may not only yield improved accuracy in predicting those at risk, but may also provide new insights into the underlying mechanisms and pathobiological networks involved in successful cognitive aging as well as detrimental aging, such as AD, and possibly herald the development of new therapeutic strategies.

SUMMARY OF THE INVENTION

The present invention relates to methods of determining if a subject has a decreased risk of suffering from future memory impairment. The methods comprise analyzing at least one plasma sample from the subject to determine a value of the subject's metabolite profile and comparing the value of the subject's metabolite profile with the value of a normal metabolite profile. A change in the value of the subject's metabolite profile, over or under normal values is indicative that the subject has a decreased risk of suffering from future memory impairment compared to a normal individual.

DETAILED DESCRIPTION OF THE INVENTION

Figure 1A:
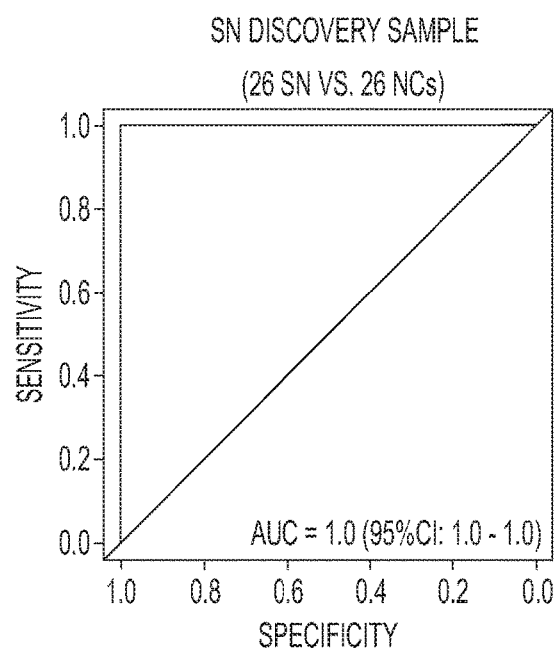
FIG. 1 depicts the results of ROC analysis using the 12-metabolite panel. This figure shows plots of SN vs NCs ROC analysis using the 12-metabolite panel in targeted discovery (a) and validation (b) phases and application of the 12-metabolite panel to the external aMCI/AD (c) and ConverterpreAD (d) samples. 95% confidence intervals are shaded. Crosshair on ROC plot represents optimal ROC threshold. SN=Supernormal, NCs=Normal control for supernormal sample; aMCI/AD=amnestic mild cognitive impairment and Alzheimer's disease; ConverterpreAD=Preclinical AD; NCo=Normal control for ConverterpreAD and aMCI/AD sample.

The present invention relates to methods of determining if a subject has a decreased risk of suffering from memory impairment. The methods comprise analyzing at least one plasma sample from the subject to determine a value of the subject's metabolite profile and comparing the value of the subject's metabolite profile with the value of a normal metabolite profile. A change in the value of the subject's metabolite profile, over or under normal values is indicative that the subject has a decreased risk of suffering from future memory impairment compared to a normal individual.

As used herein, the term subject or "test subject" indicates a mammal, in particular a human or non-human primate. The test subject may or may not be in need of an assessment of a predisposition to memory impairment. For example, the test subject may have a condition or may have been exposed to injuries or conditions that are associated with memory impairment prior to applying the methods of the present invention. In another embodiment, the test subject has not been identified as a subject that may have a condition or may have been exposed to injuries or conditions that are associated with memory impairment prior to applying the methods of the present invention.

As used herein, the phrase "memory impairment" means a measureable or perceivable decline or decrease in the subject's ability to recall past events. As used herein, the term "past events" includes both recent (new) events (short-term memory) or events further back in time (long-term memory). In one embodiment, the methods are used to assess a decreased risk of short-term memory impairment, or conversely, to assess the lack of an increased risk of short-term memory impairment. In another embodiment, the methods are used to assess a decreased risk in long-term memory impairment, or conversely, to assess the lack of an increased risk of long-term memory impairment. The memory impairment for which the risk, or lack thereof, is being assessed can be age-related memory impairment. The memory impairment for which the risk, or lack thereof, is being assessed may also be disease-related memory impairment. Examples of disease-related memory impairment include but are not limited to Alzheimer's Disease, Parkinson's Disease, Multiple Sclerosis, Huntington's Disease, Pick's Disease, Progressive Supranuclear Palsy, Brain Tumor(s), Head Trauma, and Lyme Disease to name a few. In one embodiment, the memory impairment for which the risk, or lack thereof, is being assessed is related to amnestic mild cognitive impairment (aMCI). In another embodiment, the memory impairment for which the risk, or lack thereof, is being assessed is related to Alzheimer's Disease.

The root cause of the memory impairment for which the risk, or lack thereof, is being assessed is not necessarily critical to the methods of the present invention. The measureable or perceivable decline in the subject's ability to recall past events may be assessed clinically by a health care provider, such as a physician, physician's assistant, nurse, nurse practitioner, psychologist, psychiatrist, hospice provider, or any other provider that can assess a subject's memory. The measureable or perceivable decline in the subject's ability to recall past events may be assessed in a less formal, non-clinical manner, including but not limited to the subject himself or herself, acquaintances of the subject, employers of the subject and the like. The invention is not limited to a specific manner in which the subject's ability to recall past events is assessed. In fact, the methods of the invention can be implemented without the need to assess a subject's ability to recall past events. Of course, the methods of the present invention may also include assessing the subject's ability to assess past events one or more times, both before determining the subject's metabolite profile after determining the subject's metabolite profile at least one time.

In one embodiment, the decline or decrease in the ability to recall past events is relative to each individual's ability to recall past events prior to the diagnosed decrease or decline in the ability to recall past events. In another embodiment, the decline or decrease in the ability to recall past events is relative to a population's (general, specific or stratified) ability to recall past events prior to the diagnosed decrease or decline in the ability to recall past events.

As used herein, the term "decreased risk" is used to mean that the test subject has a decreased chance of developing or acquiring memory impairment compared to a normal individual. The decreased risk may be relative or absolute and may be expressed qualitatively or quantitatively. For example, a decreased risk may be expressed as simply determining the subject's metabolite profile and placing the patient in a "decreased risk" category, based upon previous population studies. Alternatively, a numerical expression of the subject's decreased risk may be determined based upon the metabolite profile. As used herein, examples of expressions of a decreased risk include but are not limited to, odds, probability, odds ratio, p-values, attributable risk, metabolite index score, relative frequency, positive predictive value, negative predictive value, and relative risk.

For example, the correlation between a subject's metabolite profile and a decreased likelihood of acquiring memory impairment may be measured by an odds ratio (OR) and by the relative risk (RR). If $P(R^+)$ is the probability of not developing memory impairment for individuals with the metabolite profile (R) and $P(R^-)$ is the probability of not developing memory impairment for individuals without the metabolite profile, then the relative risk (or lack thereof) is the ratio of the two probabilities: $RR=P(R^+)/P(R^-)$.

As used herein, the term "increased risk," as used, for example, in connection with a lack of increased risk, is used to mean that the test subject has an increased chance of developing or acquiring memory impairment compared to a normal individual. The increased risk may be relative or absolute and may be expressed qualitatively or quantitatively. For example, an increased risk may be expressed as simply determining the subject's metabolite profile and placing the patient in an "increased risk" category, based upon previous population studies. Alternatively, a numerical expression of the subject's increased risk may be determined based upon the metabolite profile. As used herein, examples of expressions of an increased risk include but are not limited to, odds, probability, odds ratio, p-values, attributable risk, metabolite index score, relative frequency, positive predictive value, negative predictive value, and relative risk.

For example, the correlation between a subject's metabolite profile and the likelihood of suffering from memory impairment may be measured by an odds ratio (OR) and by the relative risk (RR). If $P(R^+)$ is the probability of developing memory impairment for individuals with the risk profile (R) and $P(R^-)$ is the probability of developing memory impairment for individuals without the risk profile, then the relative risk is the ratio of the two probabilities: $RR=P(R^+)/P(R^-)$.

In case-control studies, however, direct measures of the relative risk often cannot be obtained because of sampling design. The odds ratio allows for an approximation of the relative risk for low-incidence diseases and can be calculated: $OR=(F^+/(1-F^+))/(F^-/(1-F^-))$, where $F^+$ is the frequency of a risk profile in cases studies and $F^-$ is the frequency of risk profile in controls. $F^+$ and $F^-$ can be calculated using the metabolite profile frequencies of the study.

The lack of attributable risk (AR) can also be used to express a lack of increased risk, or even a decreased risk. The AR describes the proportion of individuals in a population exhibiting memory impairment due to a specific member of the metabolite profile. AR may also be important in quantifying the role of individual components (specific member) in disease etiology and in terms of the public health impact of the individual marker. The public health relevance of the AR measurement lies in estimating the proportion of cases of memory impairment in the population that could be prevented if the profile or individual component were absent. AR may be determined as follows: $AR=P_E(RR-1)/(P_E(RR-1)+1)$, where AR is the risk attributable to a profile or individual component of the profile, and $P_E$ is the frequency of exposure to a profile or individual component of the profile within the population at large. RR is the relative risk, which can be approximated with the odds ratio when the profile or individual component of the profile under study has a relatively low incidence in the general population.

In one embodiment, a decreased risk for a subject can be determined from p-values that are derived from association studies. Specifically, associations with specific profiles can be performed using regression analysis by regressing the metabolite profile with lack of memory impairment. In addition, the regression may or may not be corrected or adjusted for one or more factors. The factors for which the analyses may be adjusted include, but are not limited to age, sex, weight, ethnicity, geographic location, fasting state, state of pregnancy or post-pregnancy, menstrual cycle, general health of the subject, alcohol or drug consumption, caffeine or nicotine intake and circadian rhythms, and the subject's apolipoprotein E (ApoE) genotype to name a few.

Decreased risk can also be determined from p-values that are derived using logistic regression. Binomial (or binary) logistic regression is a form of regression which is used when the dependent is a dichotomy and the independents are of any type. Logistic regression can be used to predict a dependent variable on the basis of continuous and/or categorical independents and to determine the percent of variance in the dependent variable explained by the independents; to rank the relative importance of independents; to assess interaction effects; and to understand the impact of covariate control variables. Logistic regression applies maximum likelihood estimation after transforming the dependent into a "logit" variable (the natural log of the odds of the dependent occurring or not). In this way, logistic regression estimates the probability of a certain event occurring or not occurring. These analyses can be conducted with the program SAS.

SAS ("statistical analysis software") is a general purpose package (similar to Stata and SPSS) created by Jim Goodnight and N.C. State University colleagues. Ready-to-use procedures handle a wide range of statistical analyses, including but not limited to, analysis of variance, regression, categorical data analysis, multivariate analysis, survival analysis, psychometric analysis, cluster analysis, and nonparametric analysis.

Accordingly, select embodiments of the present invention comprise the use of a computer comprising a processor and the computer is configured or programmed to generate one or more metabolite profiles and/or to determine statistical risk. The methods may also comprise displaying the one or more profiles and/or risk profiles on a screen that is communicatively connected to the computer. In another embodiment, two different computers can be used: one computer configured or programmed to generate one or more metabolite profiles and a second computer configured or programmed to determine statistical risk. Each of these separate computers can be communicatively linked to its own display or to the same display.

As used herein, the phrase "metabolite profile" means the combination of a subject's metabolites found in the peripheral blood or portions thereof, such as but not limited to plasma or serum. The metabolite profile is a collection of measurements, such as but not limited to a quantity or concentration, for individual metabolites taken from a test sample of the subject. Examples of test samples or sources of components for the metabolite profile include, but are not limited to, biological fluids, which can be tested by the methods of the present invention described herein, and include but are not limited to whole blood, such as but not limited to peripheral blood, serum, plasma, cerebrospinal fluid, urine, amniotic fluid, lymph fluids, and various external secretions of the respiratory, intestinal and genitourinary tracts, tears, saliva, milk, white blood cells, myelomas and the like. Test samples to be assayed also include but are not limited to tissue specimens including normal and abnormal tissue.

Techniques to assay levels of individual components of the metabolite profile from test samples are well known to the skilled technician, and the invention is not limited by the means by which the components are assessed. In one embodiment, levels of the individual components of the metabolite profile are assessed using mass spectrometry in conjunction with ultra-performance liquid chromatography (UPLC), high-performance liquid chromatography (HPLC), gas chromatography (GC), gas chromatography/mass spectroscopy (GC/MS), and UPLC to name a few. Other methods of assessing levels of the individual components include biological methods, such as but not limited to ELISA assays.

The assessment of the levels of the individual components of the metabolite profile can be expressed as absolute or relative values and may or may not be expressed in relation to another component, a standard an internal standard or another molecule of compound known to be in the sample. If the levels are assessed as relative to a standard or internal standard, the standard may be added to the test sample prior to, during or after sample processing.

To assess levels of the individual components of the metabolite profile, a sample is taken from the subject. The sample may or may not processed prior assaying levels of the components of the metabolite profile. For example, whole blood may be taken from an individual and the blood sample may be processed, e.g., centrifuged, to isolate plasma or serum from the blood. The sample may or may not be stored, e.g., frozen, prior to processing or analysis.

Table 1 below lists an exemplary analysis of some of the metabolites. In the Table: SN=Supernormal; $NC_s$=Normal control for supernormal sample; *Significant difference between the groups for individual metabolites is not required for inclusion in the logistic regression classifier model. #Beta weights are from the overall classifier model with SN vs. $NC_s$, as the outcome and 12 metabolites collectively as the predictors for the Discovery and Validation samples. Negative Beta weights indicate lower abundance of the metabolite in the SN group compared to the $NC_s$ group, while positive Beta weights reflect greater abundance in the SN group.

TABLE 1

Natural Log Transformed Data of Discovery and Internal Validation Samples for Metabolite Panel

| Metabolite | Group | Discovery sample | | | Validation sample | | | Total sample |
|---|---|---|---|---|---|---|---|---|
| | | Mean | SD | t test* (p) | Mean | SD | t test* (p) | Beta, SE, (p)# |
| Arginine | SN | 4.16 | 0.37 | −0.84 (.41) | 4.34 | 0.51 | −1.22 (.23) | −0.17, 0.96, (.10) |
| | $NC_s$ | 4.25 | 0.40 | | 4.53 | 0.32 | | |
| C16:2-OH | SN | −4.68 | 0.24 | −1.02 (.32) | −4.68 | 0.23 | −1.74 (.10) | −0.25, 2.49, (.01) |
| | $NC_s$ | −4.61 | 0.24 | | −4.56 | 0.15 | | |
| C16:1-OH | SN | −4.59 | 0.25 | −0.38 (.70) | −4.62 | 0.25 | −2.17 (.04) | −0.05, 2.08, (.90) |
| | $NC_s$ | −4.57 | 0.18 | | −4.43 | 0.20 | | |
| Lyso PC a C17:0 | SN | 0.84 | 0.27 | −1.02 (.31) | 0.78 | 0.27 | −1.31 (.20) | −0.34, 1.70, (.004) |
| | $NC_s$ | 0.91 | 0.27 | | 0.93 | 0.37 | | |
| Asparagine | SN | 4.19 | 0.22 | −1.03 (.31) | 4.20 | 0.18 | −2.19 (.01) | −0.67, 0.88, (.001) |
| | $NC_s$ | 4.26 | 0.22 | | 4.36 | 0.21 | | |
| Lyso PC a C28:1 | SN | −0.81 | 0.29 | 1.77 (.08) | −0.75 | 0.33 | −0.90 (.38) | −0.01, 1.42, (.99) |
| | $NC_s$ | −0.93 | 0.20 | | −0.64 | 0.28 | | |
| Nitrotyrosine | SN | −0.30 | 0.18 | 0.14 (.89) | −0.18 | 0.13 | 2.86 (.007) | 0.94, 1.42, (.009) |
| | $NC_s$ | −0.31 | 0.26 | | −0.52 | 0.42 | | |
| C5 | SN | −1.99 | 0.49 | 0.90 (.37) | −2.15 | 0.34 | −0.32 (.75) | 0.10, 0.78, (.08) |
| | $NC_s$ | −2.12 | 0.50 | | −2.11 | 0.39 | | |
| Histamine | SN | −0.39 | 2.30 | −0.29 (.78) | −0.59 | 2.17 | 0.17 (.87) | 0.03, 0.13, (.81) |
| | $NC_s$ | −0.19 | 2.65 | | −0.76 | 3.41 | | |
| PC aa C38:5 | SN | 4.16 | 0.30 | 2.00 (.05) | 4.14 | 0.28 | 0.23 (.82) | 0.41, 1.87, (.001) |
| | $NC_s$ | 3.98 | 0.32 | | 4.12 | 0.28 | | |
| Aspartate | SN | 3.04 | 0.48 | 2.34 (.02) | 3.02 | 0.42 | −1.42 (.18) | 0.35, 0.88, (.15) |
| | $NC_s$ | 2.73 | 0.48 | | 3.19 | 0.23 | | |
| Citrulline | SN | 4.15 | 0.32 | 1.28 (.21) | 4.10 | 0.26 | −1.72 (.10) | 0.80, 1.91, (.009) |
| | $NC_s$ | 4.04 | 0.27 | | 4.28 | 0.28 | | |

Individual components of the metabolite profile thus include but are not limited to (1) Arginine, (2) Hydroxyhedadecadienylcarnitine (C16:2-OH), (3) 3-Hydroxypalmitoleylcarnitine (C16:1-OH), (4) Lyso PC a C17:0, (5) Asparagine, (6) Lyso PC a C28:1, (7) Nitrotyrosine, (8) Valerylcarnitine (C5), (9) Histamine, (10) PC aa C38:5, (11) Aspartate and (12) Citrulline. Metabolite C species, e.g., C3, denote acylcarnitines (ACs). Phosphocholine (PC) metabolites display combined numbers of carbon atoms for their two acyl groups (sn1 and sn2 positions), e.g., C38, whereas the combined number of double bonds (unsaturation) is displayed after the colon, e.g., C38:5. Acyl group linkages to choline backbone for PCs feature ester (a) or ether (e) linkage, e.g., PC aa C38:5.

For the purposes of using the methods of the present invention to determine if a subject has a decreased risk of suffering from future memory impairment, the metabolite profile comprises at least two, three, four, five, six, seven, eight, nine, ten, 11 or 12 of metabolites 1-12 listed above to produce a "SuperNormal metabolite profile." If two metabolites are used in generating the SuperNormal metabolite profile, any combination of the two listed above can be used. If three metabolites are used in generating the SuperNormal metabolite profile, any combination of three of the metabolites listed above can be used. If four metabolites are used in generating the SuperNormal metabolite profile, any combination of four of the metabolites listed above can be used. If five metabolites are used in generating the SuperNormal metabolite profile, any combination of five of the metabolites listed above can be used. If six metabolites are used in generating the SuperNormal metabolite profile, any combination of six of the metabolites listed above can be used. If seven metabolites are used in generating the SuperNormal metabolite profile, any combination of seven of the metabolites listed above can be used. If eight metabolites are used in generating the SuperNormal metabolite profile, any combination of eight of the metabolites listed above can be used. If nine metabolites are used in generating the SuperNormal metabolite profile, any combination of nine of the metabolites listed above can be used. If ten metabolites are used in generating the SuperNormal metabolite profile, any combination of ten of the metabolites listed above can be used. If 11 metabolites are used in generating the SuperNormal metabolite profile, any combination of 11 of the metabolites listed above can be used. Of course, all 12 metabolites can be used in generating the SuperNormal metabolite profile.

In another embodiment, the signs (positive or negative) can be reversed for one or more of metabolites 1-12 above, and this "reverse metabolic profile" can be used to determine in a subject has an increased risk of suffering from future memory impairment. For the purposes of using the methods of the present invention to determine if a subject has an increased risk of suffering from future memory impairment, the reverse metabolite profile comprises at least two, three, four, five, six, seven, eight, nine, ten, 11 or 12 of metabolites 1-12 listed above. If two metabolites are used in generating the reverse metabolite profile, any combination of the two listed above can be used. If three metabolites are used in generating the reverse metabolite profile, any combination of three of the metabolites listed above can be used. If four metabolites are used in generating the reverse metabolite profile, any combination of four of the metabolites listed above can be used. If five metabolites are used in generating the reverse metabolite profile, any combination of five of the metabolites listed above can be used. If six metabolites are used in generating the reverse metabolite profile, any combination of six of the metabolites listed above can be used. If seven metabolites are used in generating the reverse metabolite profile, any combination of seven of the metabolites listed above can be used. If eight metabolites are used in generating the reverse metabolite profile, any combination of eight of the metabolites listed above can be used. If nine metabolites are used in generating the reverse metabolite profile, any combination of nine of the metabolites listed above can be used. If ten metabolites are used in generating the reverse metabolite profile, any combination of ten of the metabolites listed above can be used. If 11 metabolites are used in generating the reverse metabolite profile, any combination of 11 of the metabolites listed above can be used. Of course, all 12 metabolites can be used in generating the reverse metabolite profile.

One or more of metabolites 1-12 used above to generate the reverse metabolite profile can be combined with one or more of metabolites of (13) propionyl AC, (14) lyso PC a C18:2, (15) PC aa C36:6, (16) PC aa C38:0, (17) PC aa C38:6, (18) PC aa C40:1, (19) PC aa C40:2, (20) PC aa C40:6 and (21) PC ae C40:6 to create a "converter metabolite profile" that can also be used to determine if a subject has an increased risk of suffering future memory impairment.

In one embodiment, the individual levels of each of the metabolites are higher than those compared to normal levels. In another embodiment, one, two, three, four, five, six, seven, eight, nine, ten, 11, 12, 13, 14, 15, 16, 17, 18, 19, 20 or 21 of the levels of each of the members of the converter metabolite profile are higher than normal levels while others, if any, are lower than or unchanged from normal levels. In another embodiment, the individual levels of each of the members of the converter metabolite are lower than those compared to normal levels. In another embodiment, one, two, three, four, five, six, seven, eight, nine, ten, 11, 12, 13, 14, 15, 16, 17, 18, 19, 20 or 21 of the levels of each of the members of the 21-metabolite panel are lower than normal levels while others, if any, are higher than or unchanged from normal levels.

The levels of depletion or augmentation of the metabolites compared to normal levels can vary. In one embodiment, the levels of any one or more of the metabolites is at least 1.05, 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20 lower than normal levels. In one embodiment, the levels of any one or more of the metabolites is at least 1.05, 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20 higher than normal levels. For the purposes of the present invention, the number of "times" the levels of a metabolite is lower or higher over normal can be a relative or absolute number of times. In the alternative, the levels of the metabolites may be normalized to a standard and these normalized levels can then be compared to one another to determine if a metabolite is lower or higher.

For the purposes of the present invention the converter metabolite profile comprises at least two, three, four, five, six, seven, eight, nine, ten, 11, 12, 13, 14, 15, 16, 17, 18, 19, 20 or 21 of the metabolites listed above. If two metabolites are used in generating the converter metabolite profile, any combination of the two listed above can be used. If three metabolites are used in generating the converter metabolite profile, any combination of three of the metabolites listed above can be used. If four metabolites are used in generating the converter metabolite profile, any combination of four of the metabolites listed above can be used. If five metabolites are used in generating the converter metabolite profile, any combination of five of the metabolites listed above can be used. If six metabolites are used in generating the converter metabolite profile, any combination of six of the metabolites listed above can be used. If seven metabolites are used in generating the converter metabolite profile, any combination of seven of the metabolites listed above can be used. If eight metabolites are used in generating the converter metabolite profile, any combination of eight of the metabolites listed above can be used. If nine metabolites are used in generating the converter metabolite profile, any combination of nine of the metabolites listed above can be used. If ten metabolites are used in generating the converter metabolite profile, any combination of ten of the metabolites listed above can be used. If 11 metabolites are used in generating the converter metabolite profile, any combination of 11 of the metabolites listed above can be used. If 12 metabolites are used in generating the converter metabolite profile, any combination of 12 of the metabolites listed above can be used. If 13 metabolites are used in generating the converter metabolite profile, any combination of 13 of the metabolites listed above can be used. If 14 metabolites are used in generating the converter metabolite profile, any combination of 14 of the metabolites listed above can be used. If 15 metabolites are used in generating the converter metabolite profile, any combination of 15 of the metabolites listed above can be used. If 16 metabolites are used in generating the converter metabolite profile, any combination of 16 of the metabolites listed above can be used. If 17 metabolites are used in generating the converter metabolite profile, any combination of 17 of the metabolites listed above can be used. If 18 metabolites are used in generating the converter metabolite profile, any combination of 18 of the metabolites listed above can be used. If 19 metabolites are used in generating the converter metabolite profile, any combination of 19 of the metabolites listed above can be used. If 20 metabolites are used in generating the converter metabolite profile, any combination of 20 of the metabolites listed above can be used. Of course, all 21 metabolites can be used in generating the converter metabolite profile.

In another embodiment, the present invention provides methods of detecting future memory impairment in a subject. In specific embodiments, the subject is cognitively normal or is exhibiting no detectable symptoms of memory impairment prior to applying the methods of the present invention. Methods of detecting future memory impairment prior to the subject exhibiting detectable symptoms of memory impairment comprise determining plasma levels of one or more metabolite of metabolites 1-21 as listed herein and comparing these plasma levels to levels that are determined to be within the normal range. When each of the detected levels is below the normal levels future memory impairment is detected according to the methods of the present invention.

Techniques to assay levels of individual components of any non-lipid component of the metabolite profile from test samples are well known to the skilled technician, and the invention is not limited by the means by which the components are assessed. In one embodiment, levels of the individual components of the non-lipid portion of the profile are assessed using quantitative arrays, PCR, Northern Blot analysis, Western Blot analysis, mass spectroscopy, high-performance liquid chromatography (HPLC, high performance gas chromatography (HPGC) and the like. Other methods of assessing levels of the individual components include biological methods, such as but not limited to ELISA assays. To determine levels of metabolites, it is not necessary that an entire metabolite, e.g., a full length protein or an entire RNA transcript, be present or fully sequenced. In other words, determining levels of, for example, a fragment of protein being analyzed may be sufficient to conclude or assess that an individual component of the metabolite profile, including the lipid and non-lipid portions of the metabolite profile, being analyzed is increased or decreased. Similarly, if, for example, arrays or blots are used to determine metabolite levels, the presence/absence/strength of a detectable signal may be sufficient to assess levels of metabolites.

The subject's metabolite profile is compared to the profile that is deemed to be a normal metabolite profile. To establish the metabolite profile of a normal individual, an individual or group of individuals may be first assessed for their ability to recall past events to establish that the individual or group of individuals has a normal or acceptable memory and/or cognitive abilities. Once established, the metabolite profile of the individual or group of individuals can then be determined to establish a "normal metabolite profile." In one embodiment, a normal metabolite profile can be ascertained from the same subject when the subject is deemed to possess normal cognitive abilities and no signs (clinical or otherwise) of memory impairment. In one embodiment, a "normal" metabolite profile is assessed in the same subject from whom the sample is taken prior to the onset of measureable, perceivable or diagnosed memory impairment. That is, the term "normal" with respect to a metabolite profile can be used to mean the subject's baseline metabolite profile prior to the onset of memory impairment. The metabolite profile can then be reassessed periodically and compared to the subject's baseline metabolite profile. Thus, the present invention also includes methods of monitoring the progression of memory impairment in a subject, with the methods comprising determining the subject's metabolite profile at more than one time point. For example, some embodiments of the methods of the present invention will comprise determining the subject's metabolite profile at two, three, four, five, six, seven, eight, nine, 10 or even more time points over a period of time, such as a year, two years, three, years, four years, five years, six years, seven years, eight years, nine years or even 10 years or longer. The methods of monitoring a subject's risk of having memory impairment would also include embodiments in which the subject's metabolite profile is assessed before and/or during and/or after treatment of memory impairment. In other words, the present invention also includes methods of monitoring the efficacy of treatment of memory impairment by assessing the subject's metabolite profile over the course of the treatment and after the treatment. In specific embodiments, the methods of monitoring the efficacy of treatment of memory impairment comprise determining the subject's metabolite profile at at least one, two, three, four, five, six, seven, eight, nine or 10 or more different time points prior to the receipt of treatment for memory impairment and subsequently determining the subject's metabolite profile at at least one, two, three, four, five, six, seven, eight, nine or 10 or more different time points after beginning of treatment for memory impairment, and determining the changes, if any, in the metabolite profile of the subject. The treatment may be any treatment designed to increase a subject's ability to recall past events, i.e., improve a subject's memory or reduce the risk of suffering from memory impairment.

In another embodiment, a normal metabolite profile is assessed in a sample from a different subject or patient (from the subject being analyzed) and this different subject does not have or is not suspected of having memory impairment. In still another embodiment, the normal metabolite profile is assessed in a population of healthy individuals, the constituents of which display no memory impairment. Thus, the subject's metabolite profile can be compared to a normal metabolite profile generated from a single normal sample or a metabolite profile generated from more than one normal sample.

Of course, measurements of the individual components, e.g., concentration, ratio, log ratios etc., of the normal metabolite profile can fall within a range of values, and values that do not fall within this "normal range" are said to be outside the normal range. These measurements may or may not be converted to a value, number, factor or score as compared to measurements in the "normal range." For example, a measurement for a specific metabolite that is below the normal range, may be assigned a value or −1, −2, −3, etc., depending on the scoring system devised.

In one embodiment, the "metabolite profile value" can be a single value, number, factor or score given as an overall collective value to the individual molecular components of the profile, or to the categorical components, e.g., a phosphatidylcholine portion, an amino acid portion, etc. For example, if each component is assigned a value, such as above, the metabolite value may simply be the overall score of each individual or categorical value. For example, if 4 of the components of the metabolite profile are amino acids, and two of those components are assigned values of "−2" and two are assigned values of "+1," the amino acid portion of the metabolite profile in this example would be −2, with a normal value being, for example, "0." In this manner, the metabolite profile value could be a useful single number or score, the actual value or magnitude of which could be an indication of the actual risk of memory impairment, e.g., the "more negative" the value, the less the risk of developing memory impairment.

In another embodiment the "metabolite profile value" can be a series of values, numbers, factors or scores given to the individual components of the overall profile. In another embodiment, the "metabolite profile value" may be a combination of values, numbers, factors or scores given to individual components of the profile as well as values, numbers, factors or scores collectively given to a group of components, such as a phosphatidylcholine portion, an amino acid portion, etc. In another example, the metabolite profile value may comprise or consist of individual values, number, factors or scores for specific component as well as values, numbers, factors or scores for a group on components.

In another embodiment individual values from the metabolites can be used to develop a single score, such as a "combined metabolite index," which may utilize weighted scores from the individual component values reduced to a diagnostic number value. The combined metabolite index may also be generated using non-weighted scores from the individual component values. When the "combined metabolite index" exceeds (or drops below) a specific threshold level, determined by a range of values developed similarly from control subjects, the individual has a low risk, or lower than normal risk, of developing memory impairment, whereas maintaining a normal range value of the "combined metabolite index" may indicate a normal risk of developing memory impairment. In this embodiment, the threshold value would be or could be set by the combined metabolite index from one or more normal subjects.

In another embodiment, the value of the metabolite profile can be the collection of data from the individual measurements and need not be converted to a scoring system, such that the "metabolite profile value" is a collection of the individual measurements of the individual components of the profile.

In specific embodiments, a subject is diagnosed of having a decreased risk of suffering from memory impairment if the subject's 21, 20, 19, 18, 17, 16, 15, 14, 13, 12, 11, 10, nine, eight, seven, six, five, four, three, two or even one of the metabolites herein are at levels different that those of normal levels.

If it is determined that a subject has an decreased risk of memory impairment (or lack of increased risk), the attending health care provider may subsequently prescribe or institute a program or protocol to maintain the decreased risk of developing memory impairment. In this manner, the present invention also provides for methods of screening individuals as candidates for administering a "maintenance protocol" to maintain a decreased risk of developing memory impairment.

Similarly, the invention provides methods of monitoring the effectiveness of a treatment for memory impairment. Once a treatment regimen has been established, the methods of monitoring a subject's metabolite profile over time can be used to assess the effectiveness of a memory impairment treatment. Specifically, the subject's metabolite profile can be assessed over time, including before, during and after treatments for memory impairment. The metabolite profile can be monitored, with, for example, the normalization or decline in the values of the profile over time being indicative that a treatment protocol may showing efficacy or may lead to improvement in the subjects memory and/or cognitive abilities and/or leading to a decreased risk of suffering additional memory loss.

The invention also provides method of treating a subject for memory impairment. The methods comprise analyzing at least one sample from the subject to determine a value of the subject's metabolite profile, and comparing the value of the subject's metabolite profile with the value obtained from subjects determined to define a normal metabolite profile, to determine if the subject's metabolite profile is altered compared to a normal metabolite profile. If the profile indicates that the subject has an increased risk of suffering from future memory impairment, or is suffering from memory impairment, compared to those defined as having a normal metabolite profile, a treatment for memory impairment is administered to the subject. In specific embodiments, the metabolite profile used in the methods of treatment herein comprises determining levels of one or more components selected from the group consisting of Arginine, Hydroxyhedadecadienylcarnitine (C16:2-OH), 3-Hydroxypalmitoleylcarnitine (C16:1-OH), Lyso PC a C17:0, Asparagine, Lyso PC a C28:1, Nitrotyrosine, Valerylcarnitine (C5), Histamine, PC aa C38:5, Aspartate and Citrulline. In a specific embodiment, the metabolite profile used in the methods of treatment herein comprises determining levels of Arginine, Hydroxyhedadecadienylcarnitine (C16:2-OH), 3-Hydroxypalmitoleylcarnitine (C16:1-OH), Lyso PC a C17:0, Asparagine, Lyso PC a C28:1, Nitrotyrosine, Valerylcarnitine (C5), Histamine, PC aa C38:5, Aspartate and Citrulline.

As used herein, treatments for memory impairment include but are not limited to administration of medicaments and application of behavioral therapies. As used herein, medicaments for treatment of memory impairment include but are not limited to, cholinesterase inhibitors, memantine, caprylic acid and coconut oil, coenzyme Q10, coral calcium, Ginkgo biloba, huperzine A, omega-3 fatty acids, curcumin, vitamin E, phosphatidylserine and tramiprosate to name a few. Examples of cholinesterase inhibitors include but are not limited to donepezil, rivastigmine, and galantamine. Of course, administering treatments for memory impairment can include co-administering more than one medicament, for example a cholinesterase inhibitor and memantine, to the subject.

All patents and publications mentioned in this specification are indicative of the level of those skilled in the art to which the invention pertains. All patents and publications cited herein are incorporated by reference to the same extent as if each individual publication was specifically and individually indicated as having been incorporated by reference in its entirety.

EXAMPLES

Example 1

All participants were recruited from the communities of Rochester, NY or Irvine, CA as part of the Rochester/Orange County Aging Study ("R/OCAS). Inclusion criteria included age over 70 years, good overall physical health, visual acuity and hearing sufficient for cognitive testing, and proficiency with the English language. Exclusion criteria included major neurological or psychiatric illness including a known diagnosis of any phenotype of Mild Cognitive Impairment (MCI) or Alzheimer's disease (AD), current or recent (<1 month) use of anticonvulsants, neuroleptics, HAART, antiemetics, and antipsychotics for any reason, and serious blood disorder including chronic abnormalities in complete blood count and anemia requiring therapy and/or transfusion.

Figure 5:
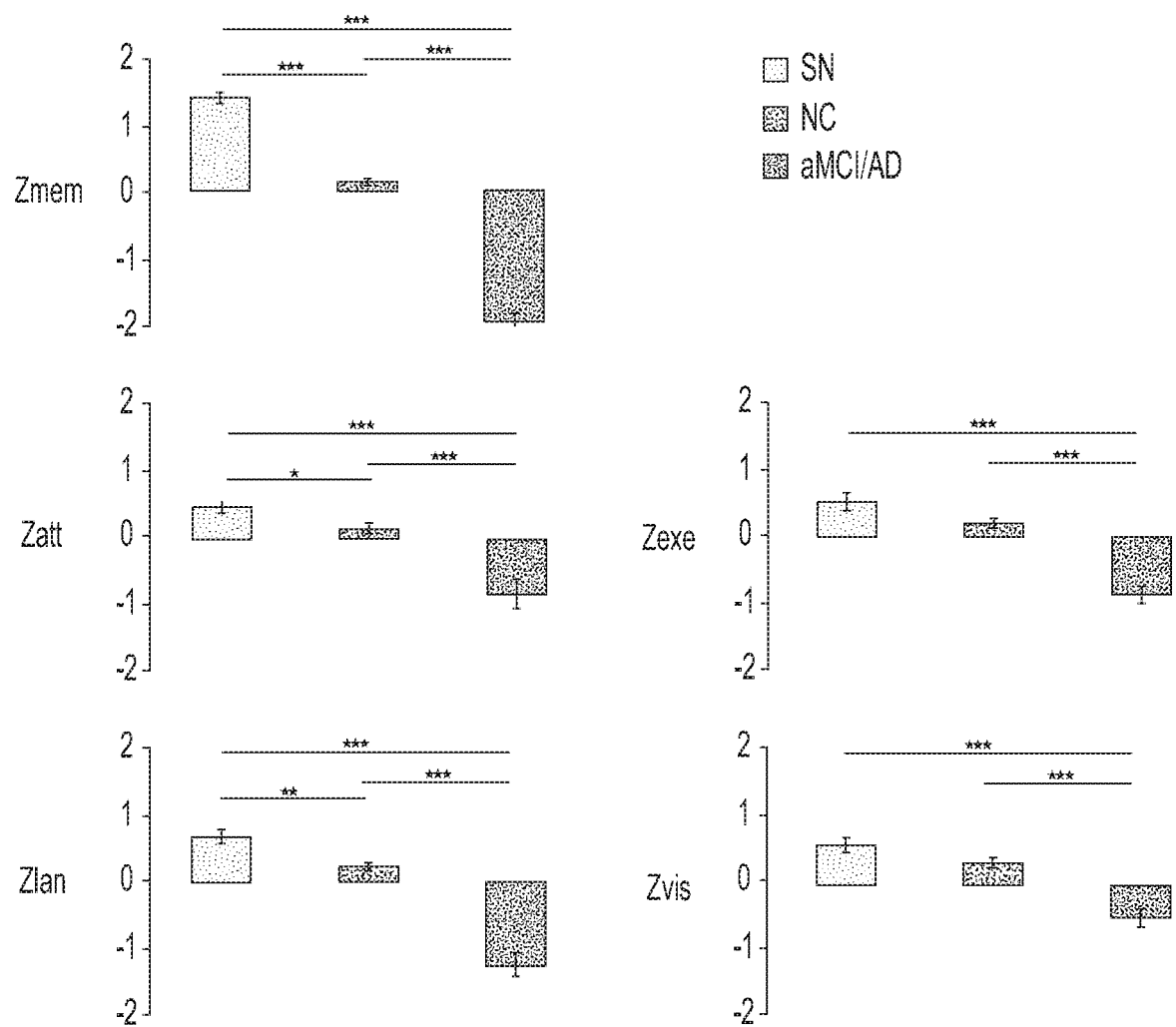
FIG. 5 depicts cognitive composite scores for the three groups (SN, NC, and aMCI/AD). Comparisons of mean values were made using ANOVA with Games-Howell post-hoc analysis. * p<0.05;  p<0.01; * p<0.001. Zmem=Memory, Zatt=Attention, Zexe=Executive function, Zlan=Language, Zvis=Visuospatial, SN=Supernormal; NC=Normal control (combined NCs and NCo); aMCI/AD=amnestic mild cognitive impairment and Alzheimer's disease.

As part of the R/OCAS, all study participants underwent yearly cognitive testing and a blood draw as close as possible to the same time and day of the year to control for circadian, seasonal, and other chronobiological effects on the cognitive testing and the blood metabolomics. All study participants underwent phlebotomy between 8 am and 10 am, while fasting and withholding their morning medications. Blood specimens were initially placed on ice and the blood components were separated within 24 hours, yielding multiple 100 mL plasma aliquots that were frozen immediately thereafter at −80° C. until undergoing metabolomic analyses. Cognitive testing was performed following the blood draw and breakfast. The cognitive battery consisted of commonly used measures administered in the standardized manner. Subjects were classified in this study using composite Z-scores based on the group characteristics adjusted for age, education, sex, and visit. Adjustment for visit could account for putative practice effects over the multi-year study. The composite cognitive domain Z-scores included attention ($Z_{att}$), executive ($Z_{exe}$), language ($Zi_{lan}$), memory ($Z_{mem}$), and visuospatial ($Z_{vis}$) as shown in Tables 2 and 3 and FIG. 5.

TABLE 2

| Attention ($Z_{att}$) | Executive ($Z_{exe}$) | Language ($Z_{lan}$) | Visuoperceptual ($Z_{vis}$) | Memory ($Z_{mem}$) |
|---|---|---|---|---|
| Wechsler Memory Scale-III Forward Digit | Wechsler Memory Scale-III Backward Digit | 1-min Category fluency (Animals) | Hooper Visual Organization Test (HVOT) | Rey Auditory Verbal Learning Test Learning |

TABLE 2-continued

| Attention ($Z_{att}$) | Executive ($Z_{exe}$) | Language ($Z_{lan}$) | Visuoperceptual ($Z_{vis}$) | Memory ($Z_{mem}$) |
|---|---|---|---|---|
| Span (WMS-III FDS) | Span (WMS-III BDS) | | | (RAVLT Learning) |
| Trail Making Test-Part A (TMT-A) | Trail Making Test-Part B (TMT-B) | Boston Naming Test 60-Item version (BNT-60) | | Rey Auditory Verbal Learning Test Retrieval (RAVLT Retrieval) Rey Auditory Verbal Learning Test Retention (RAVLT Recognition) |

TABLE 3

| Clinical/Cognitive Measures | Dependent Measure (Range) | Domain Assessed |
|---|---|---|
| Multiple Assessment Inventory IADL Scale (MAI-IADL) Lawton MP. (1988) Instrumental Activities of Daily Living (IADL) scale: Original observer-rated version. *Psychopharmacology Bulletin*, 24, 785-7. | Total Score (0-27) | Functional capacities |
| Multifactorial Memory Questionnaire (MMQ) Troyer AK and Rich JB. (2002). Psychometric properties of a new nnetannennory questionnaire for older adults. *Journal of Gerontology*, 57(1), 19-27. | Total Score (0-228) | Memory complaints |
| Mini Mental State Examination (MMSE) Folstein, MF, Folstein, SE, and McHugh, PR. (1975). "Mini-mental state". *Journal of Psychiatric Research*, 12, 189-98. | Total Score (0-30) | Global cognitive ability |
| Geriatric Depression Scale-Short Form (GDS-SF) Sheikh JI and Yesavage JA. (1986). Geriatric Depression Scale (GDS): Recent evidence and development of a shorter version. *Clinical Gerontologist*, 5, 165-173. | Total Score (0-15) | Mood |
| Wechsler Memory Scale-III Forward Digit Span (WMS-III FDS) Wechsler D. *Wechsler Memory Scale-III Manual*. San Antonio, TX: The Psychological Corporation, 1997. | Span Length (0-9) | Attention |
| Trail Making Test-Part A (TMT-A) Reitan RM. (1958). Validity of the Trail Making Test as an indicator of organic brain damage. *Perceptual and Motor Skills*, 8, 271-6. | Completion time (1-300 seconds) | Attention |
| Wechsler Memory Scale-III Backward Digit Span (WMS-III BDS) Wechsler D. *Wechsler Memory Scale-III Manual*. San Antonio, TX: The Psychological Corporation, 1997. | Span Length (0-8) | Executive ability |
| Trail Making Test-Part B (TMT-B) Reitan RM. (1958). Validity of the Trail Making Test as an indicator of organic brain damage. *Perceptual and Motor Skills*, 8, 271-6. | Completion Time (1-300 seconds) | Executive ability |
| Category fluency (Animals) Borkowski J, Benton A, Spreen O. (1967). Word fluency and brain damage. *Neuropsychologia*, 5, 135-140 | Animals named in 1-minute | Language |
| Boston Naming Test 60-Item version (BNT-60) Kaplan E, Goodglass H, and Weintraub S. (1983). Boston Naming Test. Philadelphia: Lea & Feibiger. | Total Correct (0-60) | Language |
| Rey Auditory Verbal Learning Test Learning (RAVLT Learning) Rey A. (1964). L'examen clinique en psychologie. Paris: Presses Universitaires de France. | Total words recalled over Trials 1-5 (0-75) | Verbal learning |
| Rey Auditory Verbal Learning Test Recall (RAVLT Retrieval) Rey A. (1964). L'examen clinique en psychologie. Paris: Presses Universitaires de France. | Words recalled at 20-minute delay (0-15) | Verbal retrieval |
| Rey Auditory Verbal Learning Test Retention (RAVLT Recognition) Rey A. (1964). L'examen clinique en psychologie. Paris: Presses Universitaires de France. | True positives-false positives (0-15) | Verbal retention |
| Hooper Visual Organization Test (HVOT) Hooper HE. Hooper Visual Organization Test (VOT) Los Angeles: Western Psychological Services; 1983. | Total score (0-30) | Visuoperception |

Figure 3:
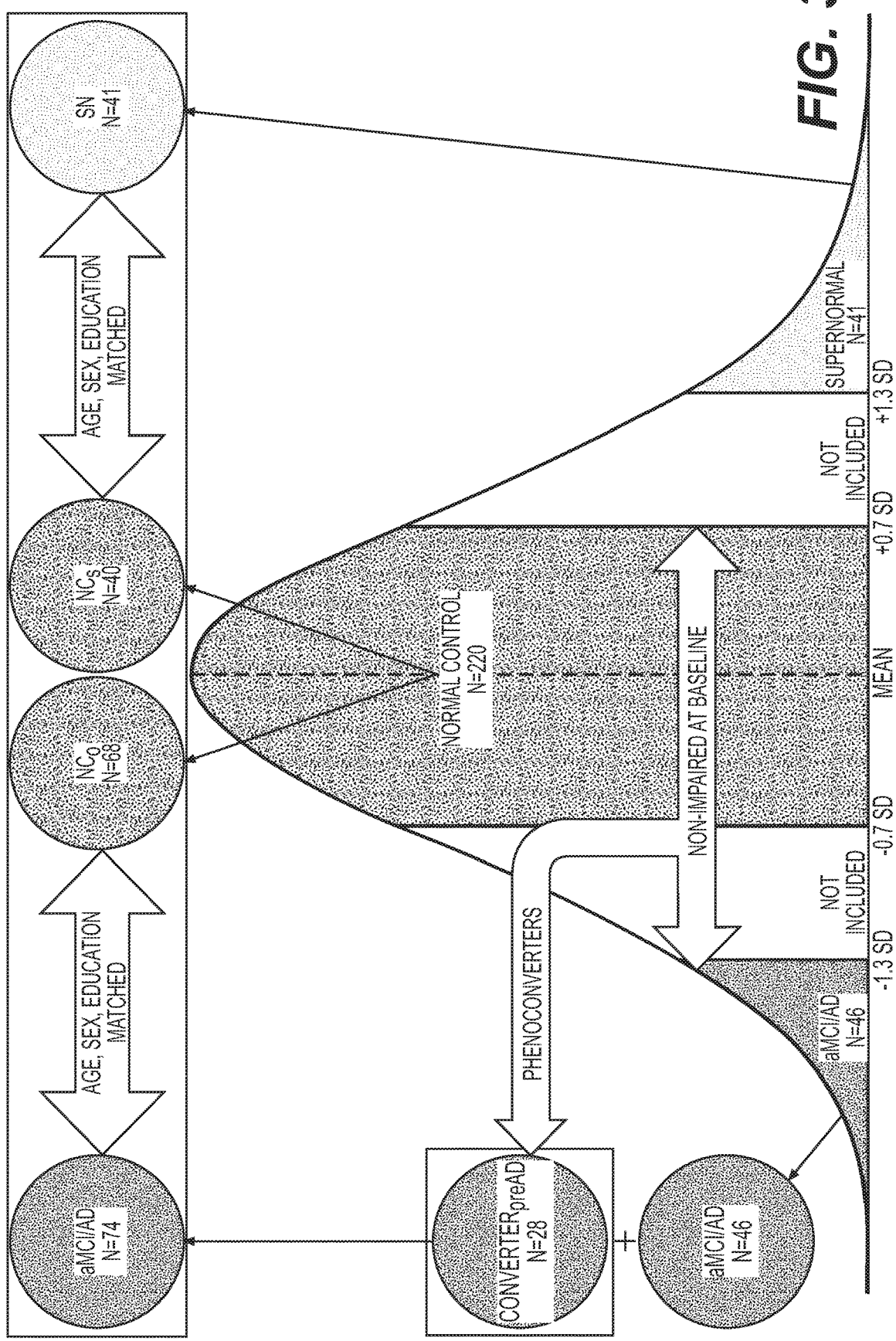
FIG. 3 depicts the selection criteria of groups from 497 available subjects. Cognitive Z-scores were fit to a robust distribution and impairment was defined as 1.3 SD below the mean. Normal control (NC) subjects had Z-scores within 0.7 SD of the group mean and stability over two consecutive visits. Supernormal (SN) subjects had memory Z-scores 1.3 SD above the group mean and non-impaired scores in all other cognitive domains. Amnestic Mild Cognitive Impairment (aMCI) and Alzheimer's disease (AD) subjects had impaired memory Z-scores, i.e., 1.3 SD below the mean. AD subjects had impairment in one other cognitive domain. Phenoconverters had non-impaired memory Z-scores at entry and impaired at a subsequent visit. Normal control groups (NCo and NCs) were matched to the aMCI/AD and SN groups based on age, education, and sex. Subjects who did not fit into these definitions (N=165) were not included in the metabolic analysis. The boxes highlight the final groups selected for analysis.

To reduce the effect of cognitively impaired participants on the mean and SD, age-, education-, sex-, and visit-adjusted residuals from each domain Z-score model were robustly standardized to have median 0 and robust SD=1, where the robust SD=IQR/1.35, as 1.35 is the IQR (Inter-Quartile Range) of a standard normal distribution. Superior memory for the supernormal (SN) group was defined as $Z_{mem} > 1.35$ SD. To further isolate successful cognitive aging, all other domain composite Z-scores were required to be >−1.35 SD. To enhance the specificity of the biomarker analyses, normal control (NC) participants in this study were conservatively defined with $Z_{mem}\pm 1$ SD of the cohort median rather than simply ≥−1.35, and all other Z-scores ≥−1.35 SD (FIG. 3). After defining the supernormal participants (SN) frequency matching was used to select, in a pseudo random manner, age-, education-, and sex-matched $NC_s$ group. After matching, one of the matched $NC_s$ subjects was found to have a hemolyzed blood sample which was unsuitable for the metabolomic analysis and thus the final dataset consisted of 41 SN and 40 $NC_s$. The clinical groups shown in Table 4 were not significantly different from each other based on age, gender, and education. ApoE status was not a significant covariate in previous metabolomic analyses and was thus not included in the present analyses.

In Table 4: SN=Supernormal; $NC_s$=Normal control for supernormal sample; aMCI/AD=amnestic mild cognitive impairment and Alzheimer's disease group; $Converter_{preAD}$=Preclinical AD; $NC_o$=Normal control for $Converter_{preAD}$ and aMCI/AD sample. The aMCI/AD, $Converter_{preAD}$, and $NC_o$ participants were included in the previous study (See Mapstone, M., et al., *Nature Medicine* 20, 415-418, doi:10.1038/nm.3466 (2014) ("Mapstone, et al."), which is incorporated by reference). [#]Baseline data for subjects who converted to aMCI/AD within 2.1 years.

LPA, 17:0 Ceramide, 12:0 LPC, 18:0 Lyso PI and PC (22:6/0:0) were procured from Avanti Polar Lipids Inc. (USA).

Targeted metabolomic analysis of plasma samples was performed using the Biocrates Absolute-IDQ P180 (BIO-CRATES, Life Science AG, Innsbruck, Austria). This validated targeted assay allows for simultaneous detection and quantification of metabolites in plasma samples (10 µL) in a high throughput manner. The plasma samples were processed as per the instructions by the manufacturer and analyzed on a triple quadrupole mass spectrometer (Xevo TQ-S, Waters Corporation, USA) operating in the MRM mode. The measurements were made in a 96 well format for a total of 148 samples, seven calibration standards and three quality control samples were integrated in the kit.

Briefly, the flow injection analysis (FIA) tandem mass spectrometry (MS/MS) method was used to quantify a panel of 144 lipids simultaneously by multiple reaction monitoring. The other metabolites were resolved on the UPLC and quantified using scheduled MRMs. The kit facilitates absolute quantitation of 21 amino acids, hexose, carnitine, 39 acylcarnitines, 15 sphingomyelins, 90 phosphatidylcholines and 19 biogenic amines. The abundance was calculated from area under the curve by normalizing to the respective isotope labeled internal standard, and differential abundance between different participant groups was computed based on

TABLE 4

Demographic Details

| Group | n | Mean Age years (SD) | Number of Male (%) | Mean Education years (SD) | Mean MMSE (SD) |
|---|---|---|---|---|---|
| SN | | | | | |
| Discovery | 26 | 82.69 (3.50) | 13 (50.0) | 15.92 (2.37) | 29.15 (1.08) |
| Validation | 15 | 84.13 (3.04) | 7 (46.7) | 17.27 (3.06) | 28.87 (1.06) |
| Total | 41 | 83.22 (3.37) | 20 (48.8) | 16.41 (2.68) | 29.05 (1.07) |
| $NC_s$ | | | | | |
| Discovery | 26 | 82.88 (3.34) | 18 (69.2) | 16.50 (2.63) | 28.68 (1.29) |
| Validation | 14 | 84.50 (4.42) | 2 (14.3) | 15.86 (2.25) | 28.62 (1.27) |
| Total | 40 | 83.45 (3.78) | 20 (50) | 16.28 (2.49) | 28.66 (1.27) |
| aMCI/AD | 74 | 82.01 (4.42) | 20 (48.8) | 15.41 (2.49) | 26.34 (2.81) |
| $Converter_{preAD\#}$ | 28 | 80.21 (4.02) | 12 (42.9) | 15.04 (2.74) | 28.61 (2.48) |
| $NC_o$ | 68 | 81.59 (3.33) | 26 (38.2) | 15.46 (2.40) | 28.67 (1.32) |

The same cognitive assessment and Z-score methods were used to define the 74 amnestic MCI (aMCI), AD and preclinical AD ($Converter_{preAD}$), and their 73 matched $NC_o$ participants and is detailed in Mapstone, et al. To preserve non-overlapping NC samples for the SN and aMCI/AD groups, five of the 73 $NC_o$ participants reported in the previous study (Mapstone, et al.) were included as $NC_s$ for the SN group. Thus 68 of the original 73 remained as $NC_o$ for the aMCI/AD group.

Example 2

LC/MS-grade acetonitrile (ACN), Isopropanol (IPA), water and methanol were purchased from Fisher Scientific (New Jersey, USA). High purity formic acid (99%) was purchased from Thermo-Scientific (Rockford, Ill). Debrisoquine, 4-Nitrobenzoic acid (4-NBA), Pro-Asn, Glycoursodeoxycholic acid, Malic acid were purchased from Sigma (St. Louis, Mo., USA). All lipid standards including 14:0 relative ratios of normalized response. The concentration is expressed as nmol/L. Human EDTA plasma samples spiked with standard metabolites were used as quality control samples to assess reproducibility of the assay. The mean of the coefficient of variation (CV) for the 180 metabolites was 0.08, and 95% of the metabolites had a CV of <0.15. The data were pre-processed using the MetIDQ software (Biocrates, Inc) prior to statistical consideration.

The procedure for metabolite selection was similar to the previous reporting in Mapstone, et al. The abundance measurements for metabolites (with a specific mass/charge ratio, m/z) were expressed as intensity units that were initially normalized using natural log transformation and subsequently by quantile normalization. To evaluate the predictive power of the metabolite panel, the discovery cohort (26 SN vs. 26 $NC_s$) was fit for deLong's test of the receiver operating characteristic (ROC) regularized logistic regression model based on the LASSO penalty. The regularization path over a grid of values was obtained for the optimizing parameter δ through N fold cross-validation to generate stable estimates. The optimal value of the tuning parameter δ was then used to estimate the penalty regression coefficients in the model. Models were fit using the "glmnet" package in R, which uses cyclical coordinate descent in a path-wise fashion. All of the individual metabolites with nonzero coefficients were retained for subsequent analysis. Twelve metabolites (Aspartate, Hydroxyhexadecadienylcarnitine, 3-Hydroxypalmitoleylcarnitine, Lyso PC a C28:1, Arginine, Valerylcarnitine, Lyso PC a C17:0, Asparagine, Citrulline, Nitrotyrosine, PC aa C38:5, and Histamine) met the specific criteria for the new panel (Table 1).

Figure 4:
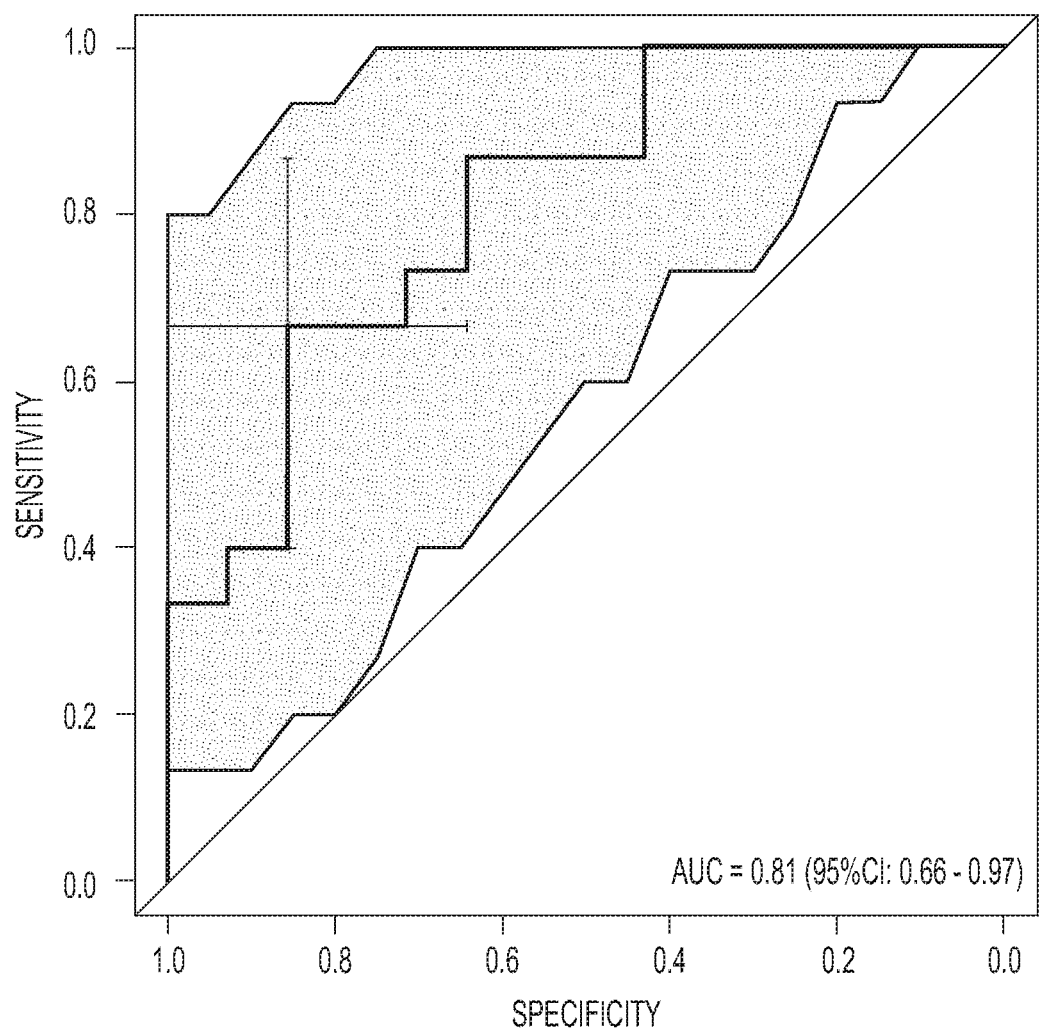
FIG. 4 depicts the results of ROC for the 7 concordant metabolites (Arginine, C16:2-OH, C16:1-OH, Lyso PC a C17:0, Asparagine, Nitrotyrosine, and PC aa C38:5) in the internal validation phase (SN=15 vs. NCs=14). The crosshairs on the ROC curve represent optimal sensitivity and specificity. The shading indicates 95% CI.

Next, the classification performance of the selected metabolites was assessed using deLong's test of area under the ROC curve (AUC), measuring the predictive accuracy separately for the discovery and validation stages. To validate the selected 12 metabolites from the discovery stage, ROC analyses were performed with the validation set of SN (n=15) and their matched $NC_s$ (n=14) as an internal validation. Given the small sample size and lack of statistical significance, the five metabolites whose levels were non-concordantly expressed in the discovery and validation stages were not excluded from the final model development. In the validation dataset, post-hoc analyses using only seven concordant metabolites resulted in a non-significant decline in AUC compared to the 12-metabolite panel (deLong's test: $|Z|=1.28$, p=0.20) lending support to the inclusion of the non-concordant metabolites (FIG. 4). The 12-metabolite panel was then applied to the combined discovery and validation groups of aMCI/AD (n=74) and Converter$_{preAD}$ (n=28) and their matched $N_o$ (n=68) from the previous study (Mapstone, et al.) (Table 5). In Table 5, the 12-metabolite panel was derived from SN vs $NC_s$ comparison. The 10-lipid panel was derived from Converter$_{preAD}$ vs $NC_o$ comparison. The 21-metabolite panel was derived from combination of 12-metabolite and 10-lipid panels. One metabolite was shared between the two panels resulting in a 21-metabolite panel instead of a 22-metabolite panel. Positive predictive value (PPV) and negative predictive value (NPV) for the optimal sensitivities and specificities were calculated using an estimated prevalence estimate of 5%. This figure was estimated from a statistical definition of supernormal which requires memory performance above one robust standard deviation factoring in normal performance in other cognitive domains.

TABLE 5

AUC (95% CI) for Subject Groups Using Different Panels

|  | SN | Converter$_{preAD}$ | aMCI/AD |
|---|---|---|---|
| 12-metabolite panel | Discovery 1.0 (1.0-1.0) Validation 0.89 (0.77-1.0) | Combined 0.92 (0.87-0.98) | Combined 1.0 (1.00-1.00) |
| 10-lipid panel | Combined 0.67 (0.56-0.79) | Discovery 0.96 (0.93-0.99) Validation 0.92 (0.87-0.98) | Discovery 0.83 (0.79-0.87) Validation 0.77 (0.69-0.84) |
| 21-metabolite panel | Combined 1.0 (1.00-1.00) | Combined 1.0 (1.00-1.00) | Combined 1.0 (1.00-1.00) |

SN = Supernormal;
Converter$_{preAD}$ = Preclinical AD;
aMCI/AD = amnestic mild cognitive impairment and Alzheimer's disease.

Next, a 12-metabolite plasma index was developed using the standardized coefficient (Beta) of each metabolite in the SN (n=41) vs $NC_s$ (n=40) logistic regression classifier model (Table 1) to weigh the natural log transformed metabolite abundance and to create a single 12-metabolite-index for all participants in the study (SN n=41, aMC/AD n=74, and combined NC n=108) (FIG. 4a). Correlations between the 12-metabolite index and the five cognitive domains ($Z_{att}$, $Z_{exe}$, $Z_{lan}$, $Z_{mem}$, $Z_{vis}$) controlling for group (SN, aMCI/AD, NC) using linear regression models were examined. Memory was the only domain significantly correlated with the 12-metabolite index (Table 6), (FIG. 4b).

TABLE 6

Linear regression of 12-metabolite index on cognitive domains controlling for group effect

| Cognitive domain | Beta | t test (p) |
|---|---|---|
| $Z_{att}$ (Attention) | 0.01 | 0.16 (0.87) |
| $Z_{exe}$ (Executive) | 0.11 | 1.76 (0.08) |
| $Z_{lan}$ (Language) | 0.04 | 0.68 (0.50) |
| $Z_{mem}$ (Memory) | 0.09 | 2.30 (0.022) |
| $Z_{vis}$ (Visuospatial) | 0.06 | 0.88 (0.38) |

ROC analysis was used to examine the 10-lipid panel in distinguishing the SN from their $NC_s$ group. Because this analysis suggested little evidence of neurodegeneration in the SN group (AUC=0.67, 95% CI:0.56-0.79), the combination of the two independently discovered and validated panels (10 lipids and 12 metabolites) was examined to distinguish the SN from $NC_s$, and both the aMCI/AD and Converter$_{preAD}$ from $NC_o$ The combined panels improved the discrimination of the SN vs $NC_s$, from AUC=0.89 (95% CI:0.77- 1.0) with the 12-metabolite panel to AUC=1.0 (95% CI:1.0-1.0) and the Converter$_{preAD}$ vs $NC_o$ from AUC=0.92 (95% CI:0.87-0.98) with the 10-lipid panel to AUC=1.0 (95% CI:1.0-1.0) (Table 5, above). The increase in classification accuracy for the Converter$_p$reAD vs NC0 groups was statistically significant (deLong's test: $|Z|=2.17$, p=0.03) underscoring the additional contribution of the 12-metabolite memory panel to defining the preclinical AD state.

Figure 1B:
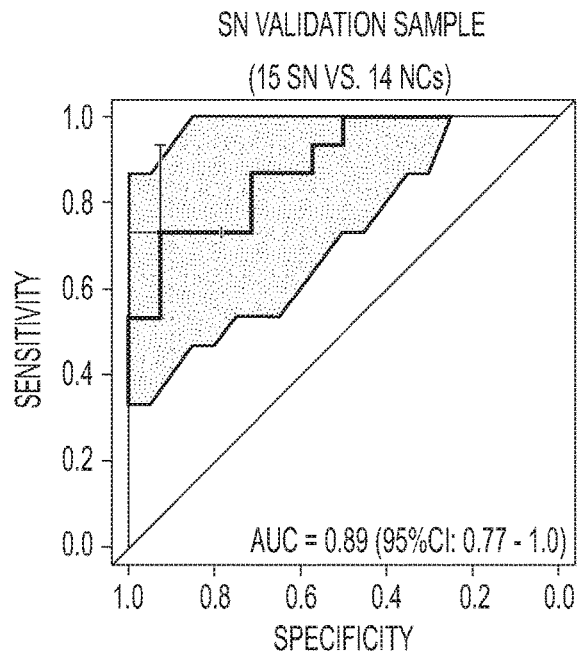

An untargeted analysis was performed on plasma from ⅔ of the SN and NCs participants (n=26 in each group) while the remaining samples from each group were reserved for an internal validation phase. The relative abundance measurement of lipid, amino acid, and biogenic amine metabolites for the two groups was performed using multiple reaction monitoring (MRM) stable isotope dilution-mass spectrometry (SID-MS). Group classification models were developed using the least absolute shrinkage selection operator (LASSO) and emphasizing selection of annotated metabolites which classified the two groups (SN vs NCs) with the greatest accuracy. LASSO was implemented using an N folds design to generate the most stable estimates of effect in the discovery phase at the cost of computational intensity. The targeted analysis revealed a set of 12 metabolites (Table 1) that, when combined in a logistic regression classifier model, produced a receiver operating characteristic (ROC) area under the curve (AUC) of 1.0 [95% CI: 1.0-1.0] (FIG. 1a) indicating perfect classification of the SN and NCs groups. At the optimal threshold, sensitivity was 1.0, specificity was 1.0, positive predictive value (PPV) was 1.0, and negative predictive value (NPV) was 1.0. Recognizing that this is naturally over fitting by design, the model was applied to the reserved validation group samples whose group membership was blinded to the statistical team. Here, the classifier model produced a ROC AUC of 0.89 [95% CI:0.77-1.0] indicating very good separation of the SN and NCs (FIG. 1b). Model fit was confirmed using the Hosmer-Lemeshow test run at 10 folds in the discovery and validation groups separately, which showed good calibration (p values>0.05). In the validation phase, sensitivity was 0.93, specificity was 0.73, PPV was 0.92 and NPV was 0.76.

Figure 1C:
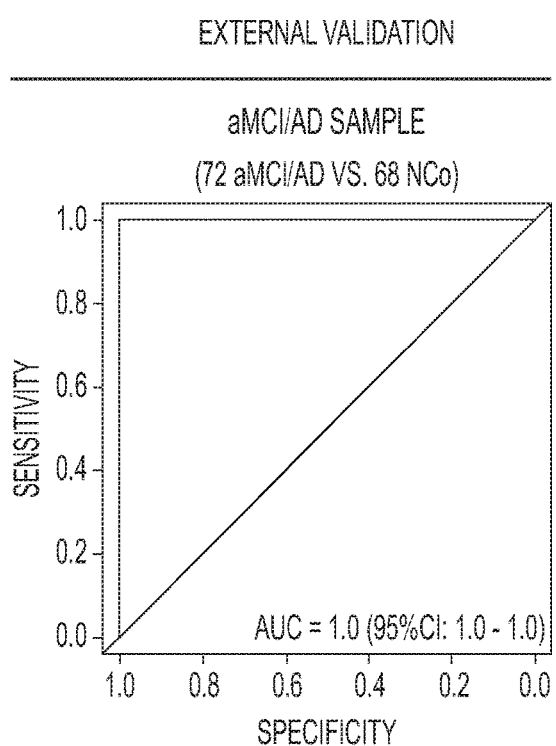
Figure 1D:
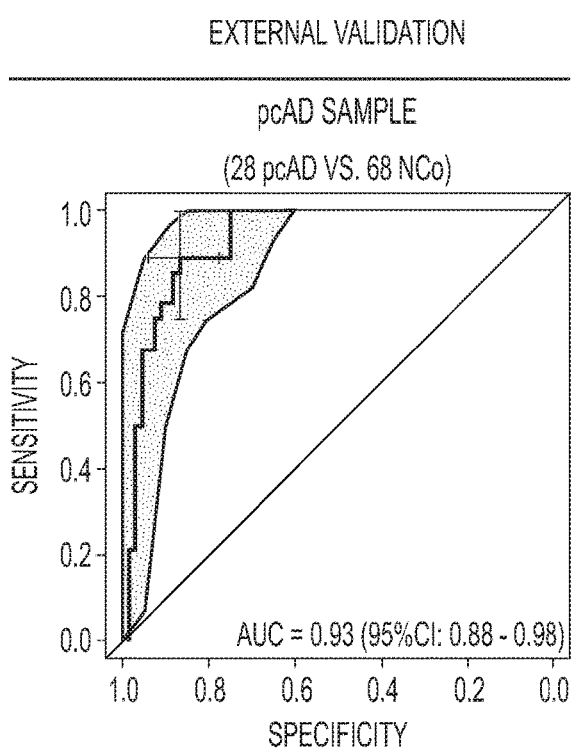
Figures 2A, 2B:
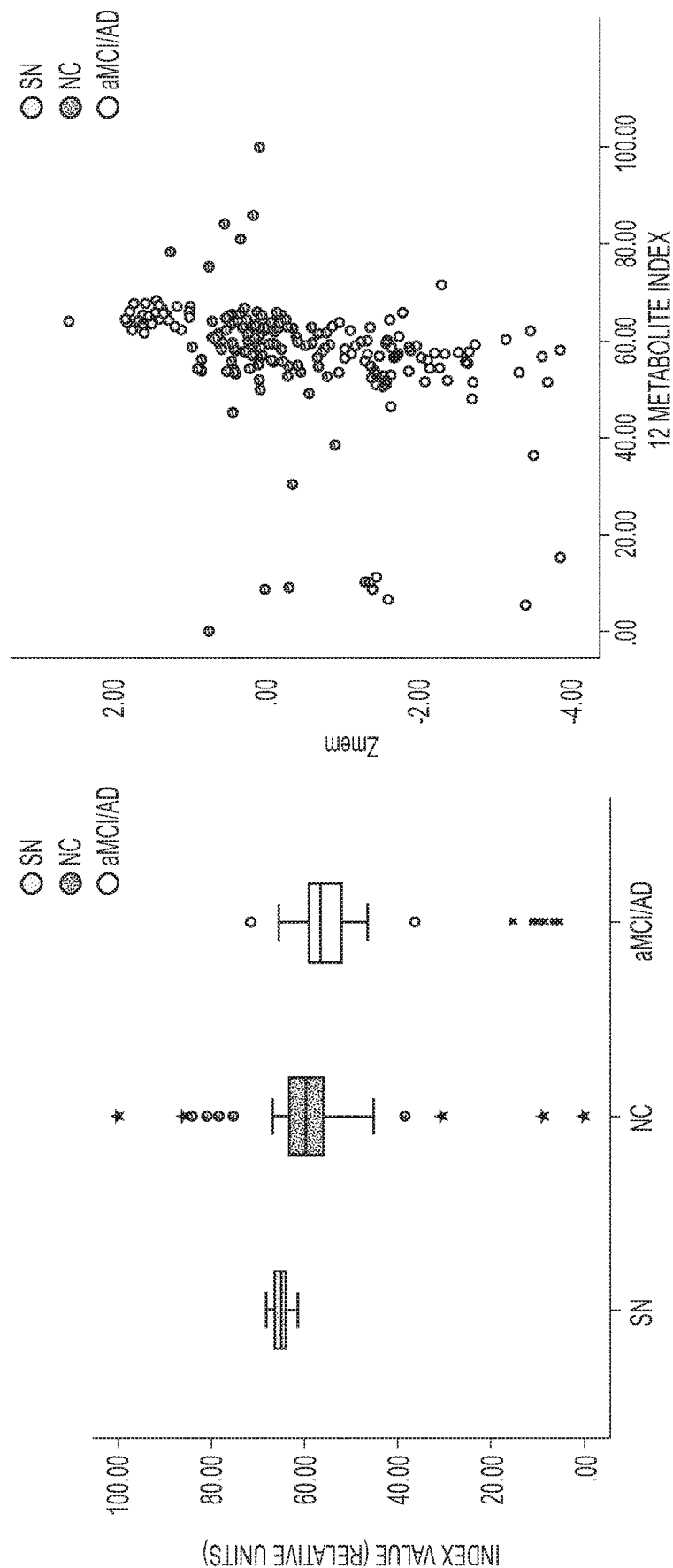
FIG. 2 depicts a 12-metabolite index and relationship with memory performance. This figure shows the derived 12-metabolite index for the three groups (SN, NCs, and aMCI/AD) (a). Box-plot for index values between groups. Using multinomial logistic regression, the 12-metabolite index significantly differentiated between SN, NC, and a MCI/AD (all $p<0.013$). The relationship between the 12-metabolite index and memory composite z-score is shown for each group of participants in the study (b).  $p<0.01$; * $p<0.001$. Zmem=Memory composite score; SN=Supernormal; NC=Normal control (combined NCs and NCo); aMCI/AD=amnestic mild cognitive impairment and Alzheimer's disease.

While the generation of the 12-metabolite panel was able to classify individuals with enhanced memory function, this same panel was used to determine if it could also discriminate individuals with impaired cognition. In particular, reversing the signs for each of the individual metabolite values in the 12-metabolite panel was used to perform a ROC analysis of 74 participants with amnestic mild cognitive impairment (aMCI) or early AD (aMCI/AD) and 68 age-, education-, and sex-matched NCo with average memory from a previous study (Mapstone et al.). Of note, the control groups matched to the SN and aMCI/AD participants were non-overlapping (Table 4). The 12 metabolite classifier model produced a ROC AUC of 1.0 [95% CI:1.0-1.0] (FIG. 1c) indicating perfect classification of the memory impaired aMCI/AD group and their cognitively normal controls. The 12-metabolite classifier model was applied to 28 preclinical aMCI/AD participants who phenoconverted from normal cognition at entry in the Mapstone, et al. study (ConverterpreAD) to aMCI or AD on average 2.1 years later (ConverterpostAD). The 12-metabolite classifier model produced a ROC AUC of 0.93[95% CI:0.88-0.98] for the 28 ConverterpreAD participants compared to their controls (FIG. 1d). The ConverterpreAD participants did not, by definition demonstrate memory impairment, but did so within the next several years, showing that using 12-metabolite panel can detect early physiological alterations which precede threshold for clinical detection. There was a significant relationship between the combined 12-metabolite index and memory composite Z-scores in the aMCI/AD, NC (combined NCs and NCo), and SN groups (Beta=0.09, t=2.30, p=0.022) when adjusting for group in the linear regression model (FIG. 2).

The 12 metabolite panel (metabolites 1-12) was combined with 9 additional lipids (metabolites 13-21) to generate a 21 member panel to classify the SN and the NCs groups (ROC AUC=1.0, 95% CI:1.0-1.0) and the ConverterpreAD and NCo groups (ROC AUC=1.0, 95% CI:1.0-1.0). The statistically significant improvement in classification accuracy for the ConverterpreAD vs NCo classification (Z=−2.17, p=0.02) highlights the notion of both neurodegeneration and subtle memory change in the preclinical AD state.

What is claimed is:

1. A method of treating a subject who has an increased risk of memory impairment or who has memory impairment, the method comprising administering a treatment for memory impairment to the subject,
wherein the subject is determined to have an increased risk of memory impairment or is determined to have memory impairment if the subject's concentration of each metabolite in a set of metabolites is lower as compared to a normal concentration of the metabolite;
wherein the set of metabolites comprises Arginine, Hydroxyhedadecadienylcarnitine (C16:2-OH), 3-Hydroxypalmitoleylcarnitine (C16:1-OH), Lyso PC a C17:0, Asparagine, Lyso PC a C28:1, Nitrotyrosine, Valerylcarnitine (C5), Histamine, PC aa C38:5, Aspartate, and Citrulline.

2. The method of claim 1, wherein the set of metabolites further comprises one or more of propionyl AC, lyso PC a C18:2, PC aa C36:6, PC aa C38:0, PC aa C38:6, PC aa C40:1, PC aa C40:2, PC aa C40:6, and PC ae C40:6.

3. The method of claim 1, wherein the normal concentration of the metabolite comprises the subject's concentration of the metabolite prior to the onset of memory impairment.

4. The method of claim 1, wherein the normal concentration of the metabolite comprises a concentration of the metabolite generated from a population of individuals that do not display memory impairment.

5. The method of claim 1, wherein the treatment is selected from the group consisting of cholinesterase inhibitors, memantine, caprylic acid and coconut oil, coenzyme Q10, coral calcium, Ginkgo biloba, huperzine A, omega-3 fatty acids, curcumin, vitamin E, phosphatidylserine, tramiprosates, and a combination thereof.

6. The method of claim 1, wherein the subject's concentration of each metabolite in the set of metabolites is determined from analysis of a blood sample from the subject.

7. A method of treating a subject who has an increased risk of memory impairment or who has memory impairment, the method comprising administering a treatment for memory impairment to the subject,
wherein the subject is determined to have an increased risk of memory impairment or is determined to have memory impairment if at least one sample, obtained at two or more timepoints from the subject, was analyzed to determine the subject's concentration of each metabolite in a set of metabolites, and the subject's concentration of each metabolite is lower as compared to a normal concentration of the metabolite;
wherein the set of metabolites comprises Arginine, Hydroxyhedadecadienylcarnitine (C16:2-OH), 3-Hydroxypalmitoleylcarnitine (C16:1-OH), Lyso PC a C17:0, Asparagine, Lyso PC a C28:1, Nitrotyrosine, Valerylcarnitine (C5), Histamine, PC aa C38:5, Aspartate.

8. The method of claim 7, wherein the set of metabolites further comprises one or more of propionyl AC, lyso PC a C18:2, PC aa C36:6, PC aa C38:0, PC aa C38:6, PC aa C40:1, PC aa C40:2, PC aa C40:6, and PC ae C40:6.

9. The method of claim 7, wherein the normal concentration of the metabolite comprises the subject's concentration of the metabolite prior to the onset of memory impairment.

10. The method of claim 7, wherein the normal concentration of the metabolite comprises a concentration of the metabolite generated from a population of individuals that do not display memory impairment.

11. The method of claim 7, wherein the treatment is selected from the group consisting of cholinesterase inhibitors, memantine, caprylic acid and coconut oil, coenzyme Q10, coral calcium, Ginkgo biloba, huperzine A, omega-3 fatty acids, curcumin, vitamin E, phosphatidylserine, tramiprosates, and a combination thereof.

12. The method of claim 7, wherein the sample is a blood sample.

13. The method of claim 7, wherein the sample is obtained at three or more time points over a period of two or more years.

* * * * *